United States Patent
Bonrath et al.

(10) Patent No.: US 8,383,837 B2
(45) Date of Patent: Feb. 26, 2013

(54) REACTION WITH A GOLD CATALYST

(75) Inventors: Werner Bonrath, Freiburg (DE);
Jocelyn Fischesser, Wittenheim (FR)

(73) Assignee: DSM IP Assets B.V., Heerlen (NL)

(*) Notice: Subject to any disclaimer, the term of this patent is extended or adjusted under 35 U.S.C. 154(b) by 428 days.

(21) Appl. No.: 12/600,859

(22) PCT Filed: Jun. 5, 2008

(86) PCT No.: PCT/EP2008/004485
§ 371 (c)(1),
(2), (4) Date: May 7, 2010

(87) PCT Pub. No.: WO2008/148549
PCT Pub. Date: Dec. 11, 2008

(65) Prior Publication Data
US 2010/0217017 A1   Aug. 26, 2010

(30) Foreign Application Priority Data
Jun. 5, 2007 (EP) .................................. 07011032

(51) Int. Cl.
| | |
|---|---|
| C07D 307/00 | (2006.01) |
| C07D 307/02 | (2006.01) |
| C07D 307/62 | (2006.01) |
| C07C 63/00 | (2006.01) |
| C07C 51/16 | (2006.01) |
| C07C 51/00 | (2006.01) |

(52) U.S. Cl. ........ 549/315; 549/295; 549/299; 562/538; 562/405; 562/407

(58) Field of Classification Search .............. 536/123.13, 536/124; 562/515, 537, 538, 405, 407; 549/315, 549/295, 299
See application file for complete search history.

(56) References Cited

U.S. PATENT DOCUMENTS

| | | | | |
|---|---|---|---|---|
| 4,816,606 A | * | 3/1989 | Brenner et al. | 568/402 |
| 2009/0221849 A1 | * | 9/2009 | Begli et al. | 562/537 |

FOREIGN PATENT DOCUMENTS

| | | |
|---|---|---|
| CS | 272 741 | 2/1991 |
| JP | 2005-154302 | * 6/2005 |
| JP | 2005-154302 | 6/2006 |
| WO | 2004/099114 | 11/2004 |
| WO | 2007/017157 | 2/2007 |

OTHER PUBLICATIONS

International Search Report for PCT/EP2008/004485, mailed Jan. 22, 2009.
Hronec et al., "Competitive Oxidation of Alcohols in Aqueous Phase using Pd/C Catalyst", Journal of Molecular Catalysis, vol. 83, 1993, pp. 75-82. XP002488297.
Biella et al., "Application of Gold Catalysts to Selective Liquid Phase Oxidation", catalysis Today, Elsevier, vol. 72, No. 1-2, Jan. 1, 2002, pp. 43-49, XP002385478.
Biella et al., "Selective Oxidation of D-Glucose on Gold Catalyst", Journal of Catalysis, Academic Press, Duluth, MN, US, vol. 206, No. 2, Mar. 10, 2002, pp. 242-247, XP004445070.
Corti et al., "Press Towards the Commercial Application of Gold Catalysts", Topics in Catalysis, Kluwer Academic Publishers-Plenum Publishers, NE, vol. 44, No. 1-2, Jun. 1, 2007, pp. 331-343, XP019509112.
Prati et all. "New Gold Catalysts for Liquid Phase Oxidation", Gold Bulletin, vol. 32, No. 3, 1999, pp. 95-101, XP002488296. (Not included).
Prati et al, "New Gold Catalysts for Liquid Phase Oxidation", Gold Bulletin, vol. 32, No. 3, 1999, pp. 96-101, XP002488296.

* cited by examiner

Primary Examiner — Taylor Victor Oh
(74) Attorney, Agent, or Firm — Nixon & Vanderhye P.C.

(57) ABSTRACT

The invention relates to a process for the catalytic conversion of a carbohydrate, an alcohol, an aldehyde or a polyhydroxy compound in the presence of a catalyst containing gold in a solvent.

19 Claims, No Drawings

REACTION WITH A GOLD CATALYST

This application is the U.S. national phase of International Application No. PCT/EP2008/004485, filed 5 Jun. 2008, which designated the U.S. and claims priority to European Application No. 07011032.5, filed 5 Jun. 2007, the entire contents of each of which are hereby incorporated by reference.

The invention relates to a process for the catalytic conversion of a carbohydrate, an alcohol, an aldehyde or a polyhydroxy compound in the presence of a catalyst containing gold in a solvent.

In many industrial processes, the conversion, e.g. the oxidation, of carbohydrates, alcohols, aldehydes or polyhydroxy compounds in aqueous phase plays a decisive role and often forms the critical stage of synthesis processes.

Thus, for example, the D-gluconic acid required for many industrial applications is prepared by an oxidation of D-glucose, which is carried out as a microbial oxidation using *Aspergillus niger*.

A further important oxidation is the formation of 2-keto-L-gulonic acid from sorbose as intermediate step in the preparation of ascorbic acid (vitamin C). The classical Reichstein process here provides a 2-stage reaction in which, in a complex manner an L-sorbofuranose is formed, which is then oxidized to 2-keto-L-gulonic acid, for example by an electrochemical method or catalytically using nickel oxide.

The hydrogenation of reducing mono- and disaccharides with supported noble metal catalysts is described in DE 19523008 A1. For industrial production, i.e. on a large scale designed for large conversions, such catalysts are, however, unsuitable, meaning that Raney nickel catalysts generally have to be used on an industrial scale.

It is therefore in principle known, e.g. from EP 0 201 957 A2, WO 97/34861, U.S. Pat. No. 5,643,849 or tetrahedron letters 38 (1997), 9023-9026, to carry out such reactions, in particular oxidations, catalytically, in particular using noble metal catalysts, mild reaction conditions with regard to the pH and the reaction temperature being made possible. Particularly suitable catalyst metals here are platinum, but also palladium and possibly rhodium, all noble metals in principle being suitable, taking into consideration their activity and their oxygen tolerance.

U.S. Pat. No. 4,599,446 describes a process for the preparation of 2-keto-L-gulonic acid by oxidizing L-sorbose with an oxygen-containing gas in water used as the solvent and in the presence of a carrier supported catalyst containing, based on the weight of the carrier, 1-10% of platinum and/or palladium and 0.5-8% of lead or bismuth, the reaction being carried out with the pH of the reaction fluid kept within the range of 6 to 8

U.S. Pat. No. 6,894,160 describes a process for the catalytic conversion of carbohydrates, alcohols, aldehydes or polyhydroxy compounds in aqueous phase, which comprises carrying out the conversion using polymer-coated metal particles with a total diameter in a range from 3-200 nm as a metal-catalyst wherein the conversion is an oxidation, wherein said process comprises the steps of: mixing the compound to be oxidized with the nanoparticles in an aqueous solution, introducing oxygen, conducting the oxidation, and separating off the oxidation products obtained.

To ensure uniform distribution of supported catalytic particles, it has also been proposed to surround the particles with surfactants in order to achieve a uniform distribution upon application to a support. In this technology, however, the surfactant sheath is dissolved following uniform distribution of the particles in order to achieve the catalyst effect, meaning that the sole function of the surfactant is to achieve uniform distribution.

The present invention relates in particular to processes for the industrial conversion of starting materials, chosen from the group consisting of alcohols, aldehydes and/or polyhydroxy compounds, such as carbohydrates, carbohydrate derivatives, starch hydrolysates, in particular mono-, di- or trisaccharides, in aqueous phase, where the conversion is carried out catalytically using a metal catalyst containing gold. It may be provided also to jointly convert mixtures of said starting materials.

Being envisaged for an industrial process, it is one objective of the invention to increase the space time yield of the conversion.

In a preferred embodiment of the present invention, the conversion is an oxidation of said starting materials, carbohydrates, for example glucose, sorbose, diacetone sorbose, sucrose, maltose, lactose, starch hydrolysates and/or isomaltulose preferably being oxidized to the corresponding carbohydrate acids. Because of the very aggressive conditions during oxidations, the long-term stability observed according to the invention and the metal leaching which does not arise in this embodiment are particularly surprising.

In a further embodiment, the conversion is a reduction, in particular a hydrogenation, reducing sugars, such as, for example, glucose, fructose, xylose, sorbose, isomaltose, isomaltulose, trehalulose, maltose and/or lactose, being hydrogenated to give the corresponding sugar alcohols. In this way, it is possible, for example, to obtain isomalt, 1,1-GPM (1-O-.alpha.-D-glucopyranosyl-D-mannitol) or 1,6-GPS (6-O-.alpha.-D-glucopyranosyl-D-sorbitol) enriched mixtures from isomaltulose. Such enriched mixtures are described in DE 195 31 396 C2.

In a further embodiment, the industrial conversion of said starting materials can be a reductive amination, preference being given to reductively aminating reducing sugars, in particular glucose, fructose, xylose, sorbose, isomaltose, isomaltulose, trehalulose, maltose and/or lactose.

In a preferred embodiment, the metal catalyst can be combined with other known catalysts that are known in the art. These catalysts comprise essentially all noble metal, for example, platinum, palladium, rhodium and/or ruthenium. However, the metal catalyst can also be a catalyst which essentially consists of a base metal or comprises the latter, where the base metal can, for example, be copper and/or nickel.

In connection with the present invention, the conversion takes place in an aqueous solvent, preferably water.

The conversion is preferably taking place at a temperature of from 30-150° C.

The reaction is advantageously performed at pH of from 5 to 14.

In connection with the present invention, a polymer-coated particle is understood as meaning a metal particle around which a polymer sheath is formed, where the total diameter of the polymer-coated metal particle, as metal particle core plus sheath, is preferably in a range from 3 to 200 nanometers.

The invention provides in a particularly preferred manner that the alcohols, aldehydes or polyhydroxy compounds to be reacted, in particular carbohydrates, carbohydrate derivatives or the like are converted in aqueous solution. The concentration can vary, but in a preferred embodiment of the invention concentrations of from 1 to 15% are used. But Glucose may also be used at higher concentrations up to 60%, particularly in the form of glucose syrup.

In particular, in a further preferred embodiment, it may be provided to pass the products mentioned above converted according to the invention during the oxidation following their conversion to a product solution to an electrodialysis, and in so doing to remove and obtain the products from the resulting product solution. A particularly preferred procedure of this type is suitable, for example, for the preparation of monooxidized carbohydrates or carbohydrate derivatives and primary alcohols. Separating off the oxidation products by means of electrodialysis, for example as described in EP 0 651 734 B1, leads to virtually pure products being obtained.

The process according to the invention can thus be coupled in a preferred manner with a process and the appertaining equipment according to EP 0 651 734 B1 in order to obtain the desired products in a particularly pure form by means of electrodialysis. The teaching of EP 0 651 734 B1 is incorporated in its entirety into the disclosure content of the present teaching with regard to the electrodialysis separation described therein, and protection is also sought therefore.

If the catalyst particles according to the invention are continually used repeatedly, it must be taken into consideration that the polymer sheath around the nanoparticles is detached or consumed. According to the invention, it is therefore particularly preferred if the polymer stabilizing the nanoparticles is added to the aqueous phase continuously or at suitable time intervals in order, in this way, to ensure that the effective polymer sheath around the nanoparticles is retained.

In the process according to the invention, the nanoparticles can be immobilized in a manner known per se on a support material, i.e. supported, the support material used preferably being a porous material in continuous form or in powder form, or the polymer-stabilized nanoparticles are immobilized in a gel structure.

Suitable immobilization materials with the help of adsorption are, in particular: $Al_2O_3$, $SiO_2$, $TiO_2$, $ZrO_2$, activated carbon, polymer latex, polystyrene latex, polyacrylamide gel, Deloxan (alkylsulfonic acid polysiloxane, aminoethyl Bio-Gel P-150. Inclusion immobilization can take place in a preferred embodiment in alginates, polyvinyl-alcohol, polyurethanes or the like.

It could be advantageous in the process to use a catalyst having a BET surface area of between 50 and 2000 $m^2/g$, preferably between 70 and 1500 $m^2/g$, and more preferably between 90 and 1100 $m^2/g$.

The reaction can be performed at ambient pressure. In a special embodiment of the invention the process is performed at a pressure of 1 to 6 bar.

If, in one embodiment of the invention, supported catalysts immobilized as described above are used, the polymer-stabilized and/or supported nanoparticles according to the invention can preferably be homogeneously or inhomogeneously distributed in gels, particularly hydrogels, or else be localized on the surface. As well as the support materials aluminum oxide, silicon dioxide and/or titanium dioxide, also suitable for this purpose are activated carbon, alumosilicates and ion exchange resins or the like.

Finally, in a further embodiment, membrane arrangements are also possible in which the active component, i.e. the polymer-stabilized nanoparticles, optionally also in supported form, are applied to or between membranes (for example hollow fibers, diffusion membranes, porous membranes and flat membranes).

In a preferred embodiment, suitable polymers for protecting and coating the nanoparticles are numerous homopolymers, copolymers and, in particular, block copolymers and graft copolymers. Particular mention may be made of polyvinyl pyrrolidones and suitable derivatives, polyvinyl alcohol, polyacrylic acid, poly(2-ethyl-2-oxazoline), poly(2-hydroxypropyl methacrylate), poly(methyl vinyl ether-co-maleic anhydride), polymethacrylic acid, poly(1-vinylpyrrolidone-co-acrylic acid), poly(styrenesulfonic acid), poly(2-acrylamido-2-methyl-1-propanesulfonic acid), poly-(vinylphosphonic acid), polydiallyldimethylammonium chloride (PDADMAC), polymethacrylamidopropyltrimethylammonium chloride, poly(3-chlorohydroxypropyl-2-methacryloxyethyldimethylammonium chloride).

The catalysts according to the invention can be used, in a preferred embodiment, also as colloids/clusters, the active component being in the form of free, i.e. not immobilized, colloids or clusters. The largest arrangement of these colloids/clusters is, according to the invention, in the nanometer range, i.e. in a range from 1 nm to 20 nm. It is only essential that the colloid particles and clusters are surrounded by a protecting polymer sheath.

The catalysts can be designed according to the type of catalyst and the reactor in question, for example as spheres, beads, cylinders, hollow cylinders, meshes, powders, pressed articles, granules, hollow spheres, fibers and films. The process itself can be used in plants which operate continuously, semicontinuously or else batchwise. Depending on the catalyst used, suitable reactors are, for example, fixed-bed reactors, reactors with expanding fixed beds, moving-bed reactors, fluidized bed reactors, stirred-bed reactors, stirred tank reactors and membrane reactors. These systems can be operated with or without catalyst and/or liquid recycling. These systems can, if necessary, also be provided with suitable internals for catalyst retention, for example with cyclones, filters and membranes.

If the conversion according to the invention is an oxidation, the presence of an oxidation agent is preferred. It is very convenient that the oxidation agent can be air or oxygen itself. Naturally, mixtures of oxygen with other gases can be used in specific embodiments of the invention as well.

The raw material, or L-sorbose, is added to the water used as the solvent in such an amount as to give a concentration of 1 to 15% by weight and preferably 2 to 10% by weight. If the concentration of L-sorbose is higher than the above-described range, the reaction rate is reduced and the formation of by-products is increased, while if the concentration is lower than the above-described range, a large amount of energy is consumed for separating the product from the solvent after completion of the reaction.

As the reaction proceeds, the pH of the reaction fluid shifts from the vicinity of neutrality to an acid region because of the desired product resulting from the oxidation of L-sorbose. Since the oxidation slows down when the pH of the reaction fluid is in an acid region, it is preferable to keep the pH of the reaction fluid in the vicinity of neutrality or in a weakly alkaline region. For this purpose, an alkaline substance is added to the reaction fluid synchronously with the progress of the reaction so that the pH of the reaction fluid may be kept within the range of 5 to 14.

Useful alkaline substances include alkali metal hydroxides such as sodium hydroxide, potassium hydroxide, etc.; alkali metal carbonates or bicarbonates such as sodium carbonate, potassium carbonate, etc.; alkali metal salts of organic acids such as sodium acetate, etc.; alkali metal phosphates; and the like. Usually, an aqueous solution of such an alkaline substance is added to the reaction fluid by means of a constant delivery pump synchronized with a pH controller.

As described above the reaction is a convenient way to convert the starting materials mentioned. In a preferred embodiment the reaction products are separated from the solvent and/or the catalyst.

In the conversion of carbohydrates according to the invention useful intermediates for the production of vitamins can be obtained. As such it is a preferred embodiment of the invention to further react the reaction products of the claimed conversion to vitamins.

One particularly preferred embodiment is vitamin C.

EXAMPLES

Experiment: Au/Alumina, 40° C., Glucose

| Entry | Reactant | Cat. Nr. | Quantity | | Content | | MW | Eq. | mmol |
|---|---|---|---|---|---|---|---|---|---|
| 1 | glucose | Fluka 49139 | 1.81 | g | 99.5 | % HPLC | 180.2 | 1.0 | 10.0 |
|   | water | Lichrosolv Merck 1.15333 | 60.0 | ml | | | 18.0 | | |
| 3 | gold on Al$_2$O$_3$ | Degussa J213 XIBB/D 1% | 787.9 | mg | 1.0 | % Au | 197.0 | 0.004 | 0.04 |
|   | oxygen | Carbagas | 20 | ml/min | >99.5 | % | 16.0 | | |
| 4 | potassium hydroxide solution | Fluka 60377 | 5.2 | ml | 2.0 | M | 56.10 | | |
| 2 | gluconic acid | theoretical yield | 2.0 | g | | | 196.2 | | 10.0 |

Experiment, Au/C, 40° C., Glucose

| Entry | Reactant | Cat. Nr. | Quantity | | Content | | MW | Eq. | mmol |
|---|---|---|---|---|---|---|---|---|---|
| 1 | glucose | Fluka 49139 | 0.91 | g | 99.5 | % HPLC | 180.2 | 1.0 | 5.0 |
|   | water | Lichrosolv Merck 1.15333 | 30.0 | ml | | | 18.0 | | |
| 3 | gold on charcoal | Degussa J105 XIA/W 1% | 394.0 | mg | 1.0 | % Au | 197.0 | 0.004 | 0.02 |
|   | oxygen | Carbagas | 10 | ml/min | >99.5 | % | 16.0 | | |
| 4 | potassium hydroxide solution | Fluka 60377 | 0.5 | ml | 2.0 | M | 56.10 | | |
| 2 | gluconic acid | theoretical yield | 1.0 | g | | | 196.2 | | 5.0 |

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor 1.81 g (10 mmol) Glucose (1), 788 mg (0.04 mmol Au) catalyst (3) followed by 60 ml water were added. The suspension was stirred at 600 RPM and heated to 40° C. (internal temperature) under oxygen gas (20 ml/min.) at atmospheric pressure for 1 hour. The rate of oxygen feed was controlled by a rotameter. The pH of the reaction mixture was continuously adjusted with a 2M potassium hydroxide solution (4) to pH 9.0. After cooling (22° C.), the catalyst was separated by filtration and the cake rinsed with water. The analysis of the filtrate was performed with HPLC (BioRad Aminex HPX-87H, refractive index detector). The structure of 2 was confirmed by LC-MS (InertSil ODS 3, 210 nm).

Results

| | | |
|---|---|---|
| Weight of filtrate: | 74.2 g | |
| Gluconic acid (2): | 1.60% | |
| Glucose (1): | n.f. | |
| Conversion of 1: | 100% | |
| Yield on 2: | >99% | |

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor 0.91 g (5 mmol) Glucose (1), 394 mg (0.02 mmol Au) catalyst (3) followed by 30 ml water were added. The suspension was stirred at 600 RPM and heated to 40° C. (internal temperature) under oxygen gas (10 ml/min.) at atmospheric pressure for 120 minutes. The rate of oxygen feed was controlled by a rotameter. The pH of the reaction mixture was continuously adjusted with a 2M potassium hydroxide solution (4) to pH 9.0. After cooling (22° C.), the catalyst was separated by filtration and the cake rinsed with water. The analysis of the filtrate was performed with HPLC (BioRad Aminex HPX-87H, refractive index detector). The structure of 2 was confirmed by LC-MS (InertSil ODS 3, 210 nm).

Results

| | | |
|---|---|---|
| Weight of filtrate: | 75.29 g | |
| Gluconic acid (2): | 2.14% | |
| Glucose (1): | n.f. | |
| Conversion of 1: | 100% | |
| Yield on 2: | 82.1% | |

Experiment: Glucose, Au/Alumina, 70° C.

| Entry | Reactant | Cat. Nr. | Quantity | Content | MW | Eq. | mmol |
|---|---|---|---|---|---|---|---|
| 1 | glucose | Fluka 49139 | 1.81 g | 99.5 % HPLC | 180.2 | 1.0 | 10.0 |
|  | water | Lichrosolv Merck 1.15333 | 60.0 ml |  | 18.0 |  |  |
| 3 | gold on $Al_2O_3$ | Degussa J218 XIBB/D 1% | 787.9 mg | 1.0 % Au | 197.0 | 0.004 | 0.04 |
|  | oxygen | Carbagas | 20 ml/min | >99.5 % | 16.0 |  |  |
| 4 | sodium bicarbonate solution | Fluka 88208 | 12.5 ml | 1.0 M | 84.0 |  |  |
| 2 | gluconic acid | theoretical yield | 2.0 g |  | 196.2 |  | 10.0 |

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor 1.81 g (10 mmol) Glucose (1), 788 mg (0.04 mmol Au) catalyst (3) followed by 60 ml water were added. The suspension was stirred at 600 RPM and heated to 70° C. (internal temperature) under oxygen gas (20 ml/min.) at atmospheric pressure for 30 minutes. The rate of oxygen feed was controlled by a rotameter. The pH of the reaction mixture was continuously adjusted with a 1M sodium bicarbonate solution (4) to pH 8.5. After cooling (22° C.), the catalyst was separated by filtration and the cake rinsed with water. The analysis of the filtrate was performed with HPLC (BioRad Aminex HPX-87H, refractive index detector). The structure of 2 was confirmed by LC-MS (InertSil ODS 3, 210 nm).

Results

| Weight of filtrate: | 92.1 g |
|---|---|
| Gluconic acid (2): | .93% |
| Glucose (1): | n.f. |
| Conversion of 1: | 100% |
| Yield on 2: | 98. |

Reaction scheme

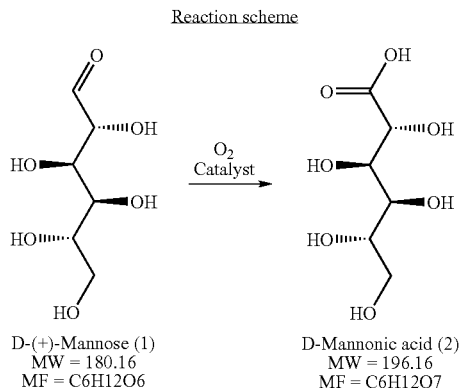 [SMILES: O=C[C@H](O)[C@H](O)[C@@H](O)[C@@H](O)CO ; O=C(O)[C@H](O)[C@H](O)[C@@H](O)[C@@H](O)CO]

D-(+)-Mannose (1)
MW = 180.16
MF = C6H12O6

D-Mannonic acid (2)
MW = 196.16
MF = C6H12O7

Experiment: Mannose, 40° C., Au/Alumina

| Entry | Reactant | Cat. Nr. | Quantity | Content | MW | Eq. | mmol |
|---|---|---|---|---|---|---|---|
| 1 | D-(+)-Mannose | Fluka 63579 | 0.91 g | 99.5 % HPLC | 180.2 | 1.0 | 5.0 |
|  | water | Lichrosolv Merck 1.15333 | 30.0 ml |  | 18.0 |  |  |
| 3 | gold on $Al_2O_3$ | Degussa J213 XIBB/D 1% | 197.0 mg | 1.0 % Au | 197.0 | 0.002 | 0.01 |
|  | oxygen | Carbagas | 20 ml/min | >99.5 % | 16.0 |  |  |
| 4 | potassium hydroxide solution | Fluka 60377 | 3.3 ml | 2.0 M | 56.10 |  |  |
| 2 | mannonic acid | theoretical yield | 1.0 g |  | 196.2 |  | 5.0 |

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor 0.91 g (5 mmol) Mannose (1), 197 mg (0.02 mmol Au) catalyst (3) followed by 30 ml water were added. The suspension was stirred at 600 RPM and heated to 40° C. (internal temperature) under oxygen gas (20 ml/min.) at atmospheric pressure for 2 hour. The rate of oxygen feed was controlled by a rotameter. The pH of the reaction mixture was continuously adjusted with a 2M potassium hydroxide solution (4) to pH 9.0. After cooling (15° C.), the catalyst was separated by filtration and the cake rinsed with water. The analysis of the filtrate was performed with HPLC (BioRad Aminex HPX-87H, refractive index detector). The structure of 2 was confirmed by LC-MS (InertSil ODS 3, 210 nm).

Results

| Weight of filtrate: | 41.27 g |
| --- | --- |
| Galactonic acid (2): | 16% |
| Galactose (1): | n.f. |
| Conversion of 1: | 100% |
| Yield of 2: | 91.0% |

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor 0.91 g (5 mmol) Galactose (1), 197 mg (0.02 mmol Au) catalyst (3) followed by 30 ml water were added. The suspension was stirred at 600 RPM and heated to 40° C. (internal temperature) under oxygen gas (20 ml/min.) at atmospheric pressure for 2 hour. The rate of oxygen feed was controlled by a rotameter. The pH of the reaction mixture was continuously adjusted with a 2M potassium hydroxide solution (4) to pH 9.0. After cooling (15° C.), the catalyst was separated by filtration and the cake rinsed with water. The analysis of the filtrate was performed with HPLC (BioRad Aminex HPX-87H, refractive index detector). The structure of 2 was confirmed by LC-MS (InertSil ODS 3, 210 nm).

Results

| Weight of filtrate: | 60.71 g |
| --- | --- |
| Galactonic acid (2): | 53% |
| Galactose (1): | n.f. |
| Conversion of 1: | 100% |
| Yield of 2: | 94.7% |

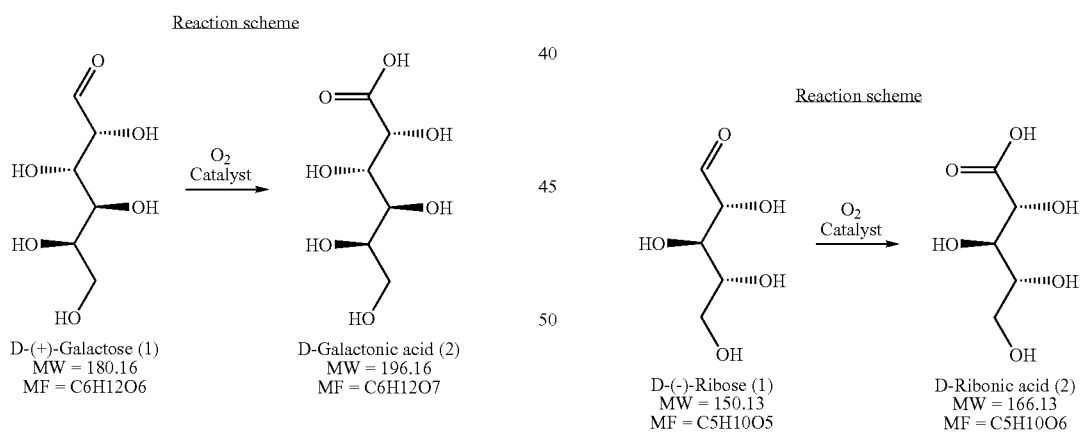

Reaction scheme

D-(+)-Galactose (1)
MW = 180.16
MF = C6H12O6

D-Galactonic acid (2)
MW = 196.16
MF = C6H12O7

Experiment: Galactose, Au/Alumina, 40° C.

Reaction scheme

D-(-)-Ribose (1)
MW = 150.13
MF = C5H10O5

D-Ribonic acid (2)
MW = 166.13
MF = C5H10O6

| Entry | Reactant | Cat. Nr. | Quantity | | Content | | MW | Eq. | mmol |
| --- | --- | --- | --- | --- | --- | --- | --- | --- | --- |
| 1 | D-(+)-Galactose | Fluka 48259 | 0.91 | g | 99.5 | % HPLC | 180.2 | 1.0 | 5.0 |
|   | water | Lichrosolv Merck 1.15333 | 30.0 | ml |   |   | 18.0 |   |   |
| 3 | gold on Al$_2$O$_3$ | Degussa J213 XIBB/D 1% | 197.0 | mg | 1.0 | % Au | 197.0 | 0.002 | 0.01 |
|   | oxygen | Carbagas | 20 | ml/min | >99.5 | % | 16.0 |   |   |
| 4 | potassium hydroxide solution | Fluka 60377 | 2.3 | ml | 2.0 | M | 56.10 |   |   |
| 2 | galactonic acid | theoretical yield | 1.0 | g |   |   | 196.2 |   | 5.0 |

Experiment

| Entry | Reactant | Cat. Nr. | Quantity | Content | MW | Eq. | mmol |
|---|---|---|---|---|---|---|---|
| 1 | D-(−)-Ribose | Fluka 83860 | 0.76 g | 99.0 % HPLC | 150.1 | 1.0 | 5.0 |
|  | water | Lichrosolv Merck 1.15333 | 30.0 ml |  | 18.0 |  |  |
| 3 | gold on $Al_2O_3$ | Degussa J218 XIBB/D 1% | 197.0 mg | 1.0 % Au | 197.0 | 0.002 | 0.01 |
|  | oxygen | Carbagas | 20 ml/min | >99.5 % | 16.0 |  |  |
| 4 | sodium bicarbonate solution | Fluka 88208 | 11.6 ml | 1.0 M | 84.0 |  |  |
| 2 | ribonic acid | theoretical yield | 0.8 g |  | 166.1 |  | 5.0 |

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor was added 0.76 g (5 mmol) Ribose (1), 197 mg (0.01 mmol Au) catalyst (3) followed by 30 ml water. The suspension was stirred at 500 RPM and heated to 40° C. (internal temperature) under oxygen gas (20 ml/min.) at atmospheric pressure for 1 hour. The rate of oxygen feed was controlled by a rotameter. The pH of the reaction mixture was continuously adjusted with a 1M sodium bicarbonate solution (4) to pH 8.5. After cooling (20° C.), the catalyst was separated by filtration and the cake rinsed with water. The analysis of the filtrate was performed with HPLC (BioRad Aminex HPX-87H, refractive index detector). The structure of 2 was confirmed by LC-MS (InertSil ODS 3, 210 nm).

Results

| | |
|---|---|
| Weight of filtrate: | 65.81 g |
| Ribonic acid (2): | 0.92% |
| Ribose (1): | n.f. |
| Conversion of 1: | 100% |
| Yiel | 73% |

Reaction scheme

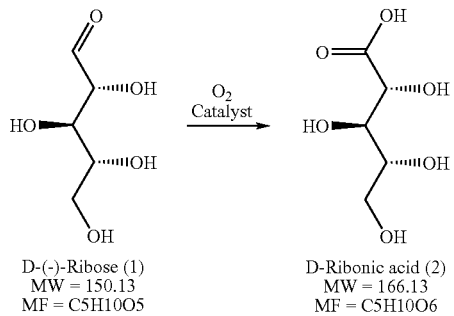

D-(−)-Ribose (1)  
MW = 150.13  
MF = C5H10O5

D-Ribonic acid (2)  
MW = 166.13  
MF = C5H10O6

Experiment: Ribose, Au/Alumina, 40° C.

| Entry | Reactant | Cat. Nr. | Quantity | Content | MW | Eq. | mmol |
|---|---|---|---|---|---|---|---|
| 1 | D-(−)-Ribose | Fluka 83860 | 0.76 g | 99.0 % HPLC | 150.1 | 1.0 | 5.0 |
|  | water | Lichrosolv Merck 1.15333 | 30.0 ml |  | 18.0 |  |  |
| 3 | gold on $Al_2O_3$ | Degussa J218 XIBB/D 1% | 197.0 mg | 1.0 % Au | 197.0 | 0.002 | 0.01 |
|  | oxygen | Carbagas | 20 ml/min | >99.5 % | 16.0 |  |  |
| 4 | sodium bicarbonate solution | Fluka 88208 | 11.6 ml | 1.0 M | 84.0 |  |  |
| 2 | ribonic acid | theoretical yield | 0.8 g |  | 166.1 |  | 5.0 |

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor 0.76 g (5 mmol) Ribose (1), 197 mg (0.01 mmol Au) catalyst (3) followed by 30 ml water were added. The suspension was stirred at 500 RPM and heated to 40° C. (internal temperature) under oxygen gas (20 ml/min.) at atmospheric pressure for 1 hour. The rate of oxygen feed was controlled by a rotameter. The pH of the reaction mixture was continuously adjusted with a 1M sodium bicarbonate solution (4) to pH 8.5. After cooling (20° C.), the catalyst was separated by filtration and the cake rinsed with water. The analysis of the filtrate was performed with HPLC (BioRad Aminex HPX-87H, refractive index detector). The structure of 2 was confirmed by LC-MS (InertSil ODS 3, 210 nm).

Results

| | |
|---|---|
| Weight of filtrate: | 65.81 g |
| Ribonic acid (2): | 0.92% |
| Ribose (1): | n.f. |
| Conversion of 1: | 100% |
| Yield | 73% |

Reaction scheme

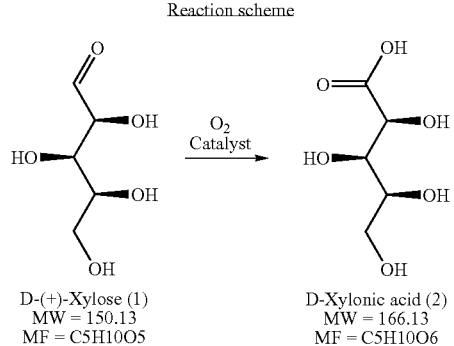 [SMILES: O=C[C@@H](O)[C@H](O)[C@@H](O)CO ; O=C(O)[C@@H](O)[C@H](O)[C@@H](O)CO]

D-(+)-Xylose (1)  
MW = 150.13  
MF = C5H10O5

D-Xylonic acid (2)  
MW = 166.13  
MF = C5H10O6

Experiment: Xylose, Au/Alumina, 40° C.

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor 0.76 g (5 mmol) Xylose (1), 197 mg (0.01 mmol Au) catalyst (3) followed by 30 ml water were added. The suspension was stirred at 500 RPM and heated to 40° C. (internal temperature) under oxygen gas (20 ml/min.) at atmospheric pressure for 1 hour. The rate of oxygen feed was controlled by a rotameter. The pH of the reaction mixture was continuously adjusted with a 1M sodium bicarbonate solution (4) to pH 8.0. After cooling (20° C.), the catalyst was separated by filtration and the cake rinsed with water. The analysis of the filtrate was performed with HPLC (BioRad Aminex HPX-87H, refractive index detector). The structure of 2 was confirmed by LC-MS (InertSil ODS 3, 210 nm).

Results

| | |
|---|---|
| Weight of filtrate: | 58.92 g |
| Xylonic acid (2): | 1.09% |
| Xylose (1) | n.f. |
| Conversion of 1: | 100% |
| Yield of 2: | 77.3% |

Table 1 gives an overview of the results (1% Au concentration by weight; all experiments yield 100% conversion on the sugar)

| Entry | Reactant | Cat. Nr. | Quantity | Content | MW | Eq. | mmol |
|---|---|---|---|---|---|---|---|
| 1 | D-(+)-Xylose | Fluka 95729 | 0.76 g | 99.0 % HPLC | 150.1 | 1.0 | 5.0 |
| | water | Lichrosolv Merck 1.15333 | 30.0 ml | | 18.0 | | |
| 3 | gold on $Al_2O_3$ | Degussa J218 XIBB/D 1% | 197.0 mg | 1.0 % Au | 197.0 | 0.002 | 0.01 |
| | oxygen | Carbagas | 20 ml/min | >99.5 % | 16.0 | | |
| 4 | sodium bicarbonate solution | Fluka 88208 | 6.1 ml | 1.0 M | 84.0 | | |
| 2 | xylonic acid | theoretical yield | 0.8 g | | 166.1 | | 5.0 |

| no | Sugar | [mmol] | Catalyst* | Support | pH | Base | T[° C.] | t[h] | Yield on 2 |
|---|---|---|---|---|---|---|---|---|---|
| 1 | glucose | 10 | J218 XIBB/D | $Al_2O_3$ | 8.5 | $NaHCO_3$ | 70 | 0.5 | 98.6 |
| 2 | glucose | 10 | J213 XIBB/D | $Al_2O_3$ | 9.0 | KOH | 40 | 1 | >99.0 |
| 3 | glucose | 10 | J105 XIA/W | Charcoal | 9.0 | KOH | 40 | 2 | 82.1 |
| 4 | ribose | 5 | J218 XIBB/D | $Al_2O_3$ | 8.5 | $NaHCO_3$ | 40 | 1 | 73.0 |
| 5 | xylose | 5 | J218 XIBB/D | $Al_2O_3$ | 8.0 | $NaHCO_3$ | 40 | 1 | 77.3 |
| 6 | galactose | 5 | J218 XIBB/D | $Al_2O_3$ | 9.0 | KOH | 40 | 2 | 94.7 |
| 7 | mannose | 5 | J218 XIBB/D | $Al_2O_3$ | 9.0 | KOH | 40 | 2 | 91.0 |

*= Degussa

In another experiment according to the invention Diacetone_L_Sorbose was oxidized with a catalyst containing gold to 2,3:4,6-Diacetone-2-ketogulonic acid Reaction scheme

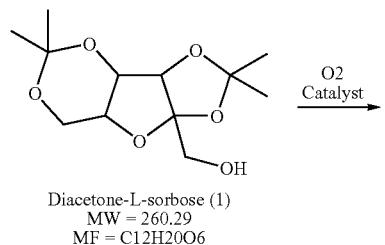

Diacetone-L-sorbose (1)
MW = 260.29
MF = C12H20O6

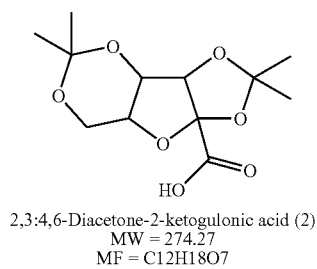

2,3:4,6-Diacetone-2-ketogulonic acid (2)
MW = 274.27
MF = C12H18O7

Experiment

Apparatus 35 ml steel autoclave

Experiment Description

In a 35-ml steel autoclave was added 6.48 g (5 mmol) DAS (1), 788 mg (0.04 mmol Au) catalyst (3) followed by 6.3 ml (5 mmol) sodium hydroxide solution (4). The suspension was stirred at 250 RPM and heated to 130° C. (internal temperature) under oxygen gas (3 bar) for 3 hours. After cooling (20° C.), the catalyst was separated by filtration and the cake rinsed with water. The analysis of the filtrate was performed with GC.

Results

| | |
|---|---|
| Weight of filtrate: | 34.8 g |
| Diacetone-Sorbose (1): | 1.31% |
| 2,3:4,6-Diacetone-2-ketogulonic acid (2): | 2.36% |
| Conversion of 1: | 65.0% |
| Yield of 2: | 59.8% |
| Selectivity: | 92.0% |

Although conversion is somewhat lower, the selectivity is very good.

In a comparative test, benzaldehyde was oxidized with a catalyst containing gold in water.

| Entry | Reactant | Cat. Nr. | Quantity | Content | MW | Eq. | mmol |
|---|---|---|---|---|---|---|---|
| 1 | DAS | Dalry, Drum 374 M1 | 6.48 g | 20.1 % GC | 260.3 | 1.0 | 5.0 |
| 3 | gold on $Al_2O_3$ | Degussa J218 XIBB/D 1% | 787.9 mg | 1.0 % Au | 197.0 | 0.008 | 0.04 |
| | oxygen | Carbagas | | >99.5 % | 16.0 | | |
| 4 | sodium hydroxide solution | Fluka 71690 | 6.3 ml | 0.8 M | 40.0 | 1.0 | 5.0 |
| 2 | DAG | theoretical yield | 1.4 g | | 274.3 | | 5.0 |

Reaction scheme

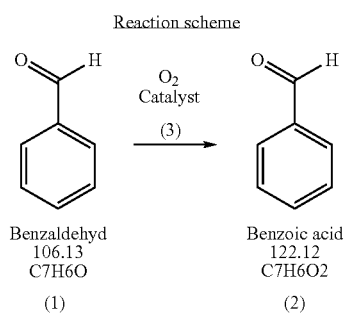 [SMILES: O=Cc1ccccc1 ; O=Cc1ccccc1]

Experiment

| Entry | Reactant | Cat. Nr. | Quantity | Content | MW | Eq. | mmol |
|---|---|---|---|---|---|---|---|
| 1 | benzaldehyd | Fluka 12010 | 2.14 g | 99.0 % GC | 106.1 | 1.0 | 20.0 |
|   | water | Lichrosolv Merck 1.15333 | 30.0 ml |   | 18.0 |   |   |
| 3 | gold on $Al_2O_3$ | Degussa J218 XIBB/D 1% | 1575.8 mg | 1.0 % Au | 197.0 | 0.004 | 0.08 |
|   | oxygen | Carbagas | 20 ml/min. | >99.5 % | 16.0 |   |   |
| 4 | potassium hydroxide solution | Fluka 60377 | 6.8 ml | 2.0 M | 56.10 |   |   |
| 2 | benzoic acid | theoretical yield | 2.4 g |   | 122.1 |   | 20.0 |

Apparatus 100 ml double jacketed reactor with circulation thermostat control (Julabo FP50-MH), IKA Eurostar Digi-Visc stirrer with propeller, reflux condenser, Pt100 thermometer/controller, Metrohm 794 dosimat with combined glass electrode, oxygen gas inlet.

Experiment Description

In a 100-ml double jacketed reactor was added 2.14 g (20 mmol) Benzaldehyd (1), 1.6 g (0.08 mmol Au) catalyst (3) followed by 30 ml water. The suspension was stirred at 1000 RPM and heated to 40° C. (internal temperature) under oxygen gas (20 ml/min.) at atmospheric pressure for 3 hours. The rate of oxygen feed was controlled by a rotameter. The pH of the reaction mixture was continuously adjusted with a 2M potassium hydroxide solution (4) to pH 8.5. After cooling (22° C.), the catalyst was separated by filtration and the cake rinsed with water. The analysis of the filtrate was performed with HPLC (BioRad Aminex HPX-87H, refractive index detector). The structure of 2 was confirmed by LC-MS (Inert-Sil ODS 3, 210 nm).

Results

| Weight of filtrate: | 214.61 g |
|---|---|
| Benzoic acid (2): | 0.59% |
| Benzaldehyde (1): | 0.33% |
| Conversion of 1: | 66.6% |
| Yield on 2: | 51.8% |
| Selectivity: | 78.2% |

In another comparative test, citral was oxidized with a catalyst containing gold in water to geranic acid.

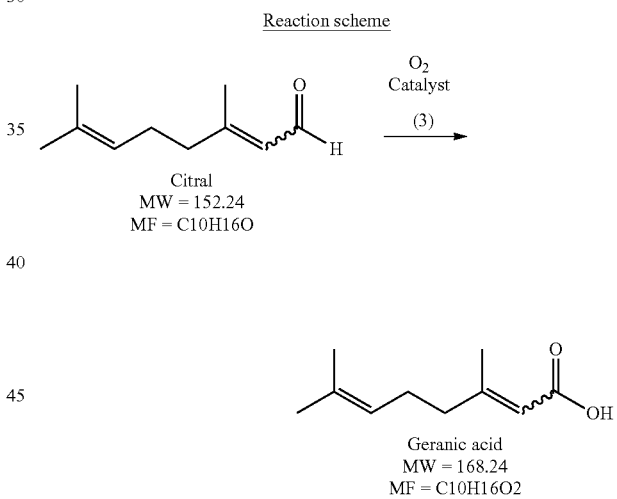

Experiment

| Entry | Reactant | Cat. Nr. | Quantity | Content | MW | Eq. | mmol |
|---|---|---|---|---|---|---|---|
| 1 | citral | Fluka 27450 | 3.21 g | 95.0 % GC | 152.2 | 1.0 | 20.0 |
|   | dichloromethane | Fluka 66740 | 15.0 ml | 99.9 % GC | 84.9 |   |   |
| 3 | gold on $Al_2O_3$ | Degussa J218 XIBB/D 1% | 393.9 mg | 1.0 % Au | 197.0 | 0.001 | 0.02 |
|   | oxygen | Carbagas | 10 bar | >99.5 % | 16.0 |   |   |
| 2 | Geranic acid | theoretical yield | 3.4 g |   | 168.2 |   | 20.0 |

Apparatus 35 ml steel autoclave

Experiment Description

In a 35-ml steel autoclave was added 3.21 g (20 mmol) Citral (1), 394 mg (0.02 mmol Au) catalyst (3) followed by 15 ml Dichloromethane. The suspension was stirred at 250 RPM and heated to 60° C. (internal temperature) under oxygen gas (10 bar) for 4 hours. After cooling (20° C.), the catalyst was separated by filtration and the cake rinsed with Dichloromethane. The mother liquor was evaporated under reduced pressure (30 mbar, 40° C.) and the resulting oil analyzed by GC-MS.

Results

| | |
|---|---|
| Weight: | 3.07 g |
| Citral (E/Z) (1): | 52.7% |
| Geranic acid (2): | 19.4% |
| Conversion of 1: | 46.9% |
| Yield of 2: | 17.4% |
| Selectivity: | 37.1% |

In both cases, the selectivity was lower and/or the conversion was reduced.

The invention claimed is:

1. A process for the catalytic conversion of a carbohydrate, an alcohol, an aldehyde or a polyhydroxy compound comprising the step of contacting the carbohydrate, the alcohol, the aldehyde or the polyhydroxy compound with a catalyst containing gold in an aqueous solvent, and wherein the catalyst is a polymer-coated particle comprising a carrier, a metallic gold or a gold salt, wherein the carrier is selected from the group consisting of aluminum oxide, silicon dioxide and titanium dioxide.

2. The process as claimed claim 1, wherein the carbohydrate is selected from the group comprising glucose, fructose, sorbose, sucrose, isomaltulose, trehalulose, maltose and lactose.

3. The process as claimed in claim 1 wherein the particle has a total diameter in a range from 3-200 nm.

4. The process as claimed in claim 1, wherein the aqueous solvent is water.

5. The process as claimed in claim 1, wherein the carbohydrate, the alcohol, the aldehyde or the polyhydroxy compound is present in a concentration of 1-15% by weight.

6. The process as claimed in claim 1, wherein the temperature during the contacting is between 30 and 150° C.

7. The process as claimed in claim 1, wherein the pH value during the contacting is between 5 and 14.

8. The process as claimed in claim 1, further comprising the step of separating the reaction products.

9. The process as claimed in claim 8, further comprising the step of reacting the reaction products to produce a vitamin.

10. The process as claimed in claim 9, wherein the vitamin is vitamin C.

11. The process as claimed in claim 1, wherein the catalyst has a BET surface area of between 50 and 2000 $m^2/g$.

12. The process as claimed in claim 1, wherein the catalyst has a BET surface area of between 70 and 1500 $m^2/g$.

13. The process as claimed in claim 1, wherein the catalyst has a BET surface area of between 90 and 1100 $m^2/g$.

14. The process as claimed in claim 1, wherein the contacting is performed in the presence of an oxidation agent.

15. The process as claimed in claim 14, wherein the oxidation agent is air or oxygen.

16. The process as claimed in claim 15, wherein the contacting is performed at a pressure between 1 to 6 bar.

17. The process according to claim 1 or 2, wherein the polymer-coated particle comprises a polymer coating which is formed of homopolymers or copolymers.

18. The process according to claim 1 or 2, wherein the polymer-coated particle comprises a polymer coating which is formed of block copolymers or graft copolymers.

19. The process according to claim 1 or 2, wherein the polymer-coated particle comprises a polymer coating which is formed of polymers selected from the group consisting of polyvinyl pyrrolidones, polyvinyl alcohol, polyacrylic acid, poly(2-ethyl-2-oxazoline), poly(2-hydroxypropyl methacrylate), poly(methylvinylether-co-maleic anhydride), polymethacrylic acid, poly(1-vinylpyrrolidone-co-acrylic acid), poly(styrenesulfonic acid), poly(2-acrylamido-2-methyl-1-propanesulfonic acid), poly-(vinylphosphonic acid), polydiallyldimethylammonium chloride and polymethacrylamidopropyl trimethylammonium chloride.

* * * * *